United States Patent [19]

Amato et al.

[11] 4,282,364

[45] Aug. 4, 1981

[54] PROCESS FOR THE PREPARATION OF THIAZOLES

[75] Inventors: Joseph S. Amato, Brooklyn, N.Y.; Sandor Karady, Mountanside; Leonard M. Weinstock, Belle Mead, both of N.J.

[73] Assignee: Merck & Co., Inc., Rahway, N.J.

[21] Appl. No.: 152,281

[22] Filed: May 22, 1980

[51] Int. Cl.$^3$ ............................................. C07D 277/25
[52] U.S. Cl. .................................... 548/202; 548/146; 424/270
[58] Field of Search ................................ 548/146, 202

[56] References Cited

U.S. PATENT DOCUMENTS

| | | | |
|---|---|---|---|
| 4,021,438 | 5/1977 | Hartman | 548/202 |
| 4,025,526 | 5/1977 | Suzuki et al. | 548/202 |
| 4,111,948 | 9/1978 | Kao et al. | |

OTHER PUBLICATIONS

Cole Bourne et al., J. Chem. Soc. 1967 pp. 685-688.
Adams, Jour. of Catalysis pp. 96-112 (1968).

*Primary Examiner*—Nicholas S. Rizzo
*Attorney, Agent, or Firm*—David L. Rose; Harry E. Westlake

[57] ABSTRACT

An improved process for the preparation of thiazoles is disclosed. The process utilizes a substituted imine and sulfur dioxide heated in the presence of a catalyst. The thiazoles are known important chemical intermediates.

11 Claims, No Drawings

PROCESS FOR THE PREPARATION OF THIAZOLES

BACKGROUND OF THE INVENTION

Many processes have been disclosed for the preparation of thiazoles owing to the importance of such compounds as chemical intermediates. One such process disclosed by Colebourne (Journal of the Chemical Society 685 (1967)) involved an imine in the presence of sulfur to prepare 4-methylthiazole. The process has the distinct disadvantage of having hydrogen sulfide, an environmental pollutant, as a by product.

SUMMARY OF THE INVENTION

The instant invention prepares thiazole compounds from imines and sulfur dioxide, avoiding the production of the hazardous by-product, hydrogen sulfide. Thus, it is an object of this invention to describe the preparation of thiazole compounds from imines and sulfur dioxide. Another object of this invention is to describe the different imines which may be used and the different thiazoles which are prepared thereby. Still another object of this invention is to describe the reaction conditions which allow the process to be carried out in a continuous fashion. A still further object of this invention is to describe the catalysts which may be utilized for this process. Further objects will become apparent upon reading the following description.

DESCRIPTION OF THE INVENTION

The process of the instant invention is best described in the following reaction scheme:

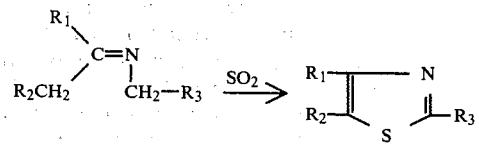

wherein $R_1$, $R_2$ and $R_3$ are independently hydrogen, loweralkyl, phenyl or substituted phenyl wherein the substituent is one or two of loweralkyl or halogen.

In the instant application, the term "loweralkyl" is intended to include those alkyl groups of either a straight or branched configuration, which contain from 1-6 carbon atoms. Exemplary of such alkyl groups is methyl, ethyl, propyl, isopropyl, butyl, sec-butyl, tert-butyl, pentyl and the like.

The term "halogen" is intended to include the halogen atoms, fluorine, chlorine, bromine or iodine.

The preferred compound prepared by the process of this invention is 4-methylthiazole, which is the compound prepared when $R_1$ is methyl and $R_2$ and $R_3$ are hydrogen.

The process for the instant reaction involves the reaction of the appropriately substituted imine (I) with sulfur dioxide in the presence of a catalyst. The reaction is carried out in the vapor phase at elevated temperatures.

In practice, a stream of a mixture of the imine and sulfur dioxide in an inert carrier gas, preferably nitrogen, is passed over the catalyst maintained at a temperature of from 400°-500° C. The preferred temperature is from 440°-480° C., with the preferred temperature for the preferred product being about 460° C. Slight temperature variations may be made to optimize the reaction conditions to a particular product.

Generally, about equal molar amounts of sulfur dioxide and the imine are employed, however, an excess of up to 10 moles of one component over the other may be employed. However, since any unreacted sulfur dioxide may be recovered from the reaction mixture and recycled, and the imine cannot be, since unreacted imine is degraded in the reactor, the use of excess imine is not economically desireable and not preferred. A slight excess of sulfur dioxide to reduce the production of imine degradation products is most preferred.

Generally, the two components are present in the reaction stream from about 2-12 mole percent of each component. It is most preferred to use about 8 mole percent of each, with perhaps a slight excess of the sulfur dioxide.

The catalyst for the instant reaction is a mixture selected from alkaline earth metal oxides, alkali metal hydroxides and zirconium oxide. The particular choice of the catalyst is not critical, since reactions catalyzed by alkaline earth metal oxides alone, or alkali metal hydroxides have been successful. However, a large improvement in the reaction occurs if an alkaline earth metal oxide is combined with zirconium oxide or if alkali metal hydroxides are combined with zirconium oxide. However, a very large and unexpected improvement in the yield, selectivity and length of useful life of the catalyst occurs, if the catalyst employed is a mixture of all three components. When all three components are employed, each one is present in the following ratios by weight. Alkaline earth metal oxide 85-98%; alkali metal hydroxide 1-15%; and zirconium oxide 0.1-2%. Preferably, the ratio is alkaline earth metal oxide 89%; alkali metal hydroxide 10%; and zirconium oxide 1%. The preferred catalyst is calcium oxide, sodium hydroxide and zirconium oxide in the above preferred ratio.

The catalyst may be supported or unsupported, however, since the catalyst is stable and non-fusible at the temperatures employed, and to insure a longer operating life between catalyst regenerations, the catalyst is preferred to be unsupported. The contact time for the reaction mixture is generally maintained at from 2-8 seconds to insure maximum reaction of the reagents and yield of the product.

The size of the reaction vessel and the amount of catalyst present is immaterial to the instant process, since larger vessels and more catalyst merely provides for a longer useful life of the catalyst before regeneration is required.

The catalyst is reusable, however, during the reaction a coating of "coke" is formed on the catalyst which presumably is a degradation product or products from the decomposition of a small amount of the imine starting materials. The catalyst is regenerated by passing steam, at reaction temperatures (400°-500° C.) over the catalyst for from 2-10 hours.

The products of the instant process are recovered generally by cooling the reaction mixture gas and vapor stream from the reactor to ambient temperatures. The thiazole condenses and is recoverable and the nitrogen carrier gas and any unreacted sulfur dioxide may be scrubbed of any imine degradation products and recycled into the reactor after being supplemented with additional sulfur dioxide and imine. It is also possible to cool the reactor effluent by passing it through water or an aqueous acid solution to disolve the thiazole. The thiazole may then be recovered from the water or aqueous acid by conventional means.

It will be appreciated that when the $R_1$ group has a methylene group attached to the imino carbon, and when the $R_1$ is different from the $R_2$—$CH_2$-group, a mixture of products may be formed. Under such conditions, the two compounds may be produced in equal or unequal amounts. However, the individual products may generally be isolated and purified using techniques known to those skilled in the art such as fractional crystallization, fractional distillation, and chromatography such as column chromatography gas-liquid chromatography, high pressure liquid chromatography and the like.

The catalyst is prepared by thoroughly mixing and fusing the components, followed by treatment which would make the fused catalyst suitable for use in the reactor. Generally after cooling the catalyst mixture, the catalyst is granulated and pulverized such that the particle size is from 18 to 36 mesh. Particle size is controlled by passing the granulated catalyst through a graduated series of sieves.

It has been found, however, that an alternate, and convenient method for the preparation of one form of the catalyst is through the use of a mixture of calcium oxide, sodium sulfate and zirconium oxide. The components are mixed in the ratios of 95 to 77% for calcium oxide; from 5 to 20% of sodium sulfate; and from 0.5 to 3% of zirconium oxide. The mixture is fused and results in a mixture of calcium sulfate, calcium oxide, sodium hydroxide and zirconium oxide. The presence of calcium sulfate does not impede the reaction; it is inert.

The imine starting materials are generally known compounds which are prepared by reacting the appropriately substituted ketone or aldehyde with an appropriately substituted amine as follows:

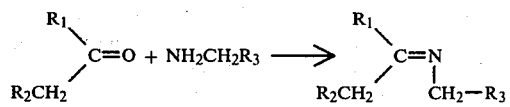

The reactants are heated together at a temperature of from 20° to 100° C. for from 2 to 20 hours either with or without an inert solvent such as toluene, benzene, and the like. The water by product is removed during the course of the reaction to force it to completion and the product is isolated using techniques known to those skilled in the art.

As noted above, the instant reaction produces the instant thiazole compounds without any polluting by-products. Prior processes resulted in the liberation of hydrogen sulfide which, if released to the atmosphere, presented a considerable environmental hazard; and if recovered, presented extra expenses in the recovery process and safe disposal. The only products prepared in the instant process are the thiazole and water. Any excess sulfur dioxide unreacted in passing through the reactor is recycled back into the inlet of the reactor. Thus, the instant process presents a considerable advantage over prior processes for the preparation of thiazoles.

The thiazoles prepared by the process of this invention are useful industrial chemicals many of which are intermediates for the preparation of other industrially and biologically active compounds. The preferred compound, 4-methylthiazole, in particular is a valuable intermediate in the preparation of thiabendazole, an important anthelmintic agent for the treatment of gastrointestinal parasites in mammals, and also an important industrial and agricultural fungicide.

The following examples are provided in order that the invention might be more fully understood. They are not meant to be limitative of the invention.

PREPARATION OF 4-METHYLTHIAZOLE

Apparatus

The reactor is housed in one chamber of a two chambered, insulated, stainless steel box. Each chamber contains a heater, attached to the bottom, which is controlled by a West 400 temperature controller. A circulating fan in each chamber distributes the heat evenly. The reactor is a nine inch, jacketed, hollow stainless steel tube, ⅜ inch in diameter and 9 inches long which is connected vertically. The catalyst is held in place by a plug of quartz wool at the bottom of the tube. Thermowells are present both in the jacket and in the catalyst bed. At the top of the tube is a three-way connector where the imine, nitrogen and sulfur dioxide streams meet before passing through the tube. The reaction stream passes out the bottom of the tube and exits the chamber through a heated pipe, to which can be connected the collection vessels. A second line splits from the exit line inside the chamber, runs into the second chamber, and is connected to a six port sampling valve. The valve is connected to a gas chromatograph allowing monitoring of the reaction. During an isolation experiment, the valve is disconnected and plugged in order to trap the entire exit stream.

Procedure (isolation reaction)

The reactor chamber is heated to 465° C. and allowed to equilibrate. (For gas-liquid chromatography monitoring the second chamber is maintained at 225° C.). Sulfur dioxide and nitrogen are then passed over the 8 ml catalyst bed for approximately 15 minutes at 11 and 96 ml/min respectively. The imine syringe pump is then turned on, pumping imine into the heated external nitrogen line at a rate of 33.3 $\mu$l/min (0.36 mmol/min). The imine vaporizes and is carried into the chamber where it mixes with the sulfur dioxide stream and passes through the tube with a contact time of 4.5 seconds The imine concentration is 7.8 mol% and the sulfur dioxide is 9.5 mol%. The exit stream passes through a glass tube with a spherical center to collect condensed material and then passes into a 4 N hydrochloric acid scrubber solution. After 180 minutes, the imine and sulfur dioxide are shut off (after passing 64.8 mmol of imine).

The condensed material is then placed in a small amount of water and extracted 3 times with methylene chloride. The scrubber solution is basified with sodium hydroxide solution and extracted three times with methylene chloride. Vapor phase chromatography of the aqueous layer shows no 4-methylthiazole remaining). The organic layers are combined, dried over magnesium sulfate and the solvent is stripped to give 3.35 g of crude material which is 90% 4-methylthiazole by vapor phase chromatography. The crude product is then vacuum distilled to give 2.95 g (46%) of material having a boiling point of 56°–60°/59 mm of Hg and the following NMR spectrum: chemical shifts are given in $\delta$ relative to tetramethylsilane in $CDCl_3$=2.45 (singlet, one proton) 6.80 (quartet, 1 proton) and 8.55 doublet, one proton).

Following the foregoing procedures, the following starting materials are prepared affording the indicated products in the given yields:

| Starting Material | Product | Yield |
|---|---|---|
| $\underset{CH_3}{\overset{C_6H_5}{>}}C=\underset{CH_3}{N}$ | $C_6H_5\underset{S}{\overset{\phantom{xx}N\phantom{xx}}{\diagdown\phantom{x}\diagup}}$ | 26% |
| $\underset{CH_3}{\overset{CH_3CH_2}{>}}C=\underset{CH_3}{N}$ | $CH_3CH_2\underset{S}{\overset{\phantom{xx}N\phantom{xx}}{\diagdown\phantom{x}\diagup}}$ + $\underset{CH_3}{\overset{CH_3}{>}}\underset{S}{\overset{\phantom{xx}N\phantom{xx}}{\diagdown\phantom{x}\diagup}}$ (3:2) | 24%(total) |
| $\underset{CH_3}{\overset{CH_3CH_2}{>}}C=\underset{CH_2CH_3}{N}$ | $CH_3CH_2\underset{S}{\overset{\phantom{xx}N\phantom{xx}}{\diagdown\phantom{x}\diagup}}$ + $\underset{CH_3}{\overset{CH_3}{>}}\underset{S}{\overset{\phantom{xx}N\phantom{xx}}{\diagdown\phantom{x}\diagup}}$ (1:1) | 29%(total) |
| $\underset{CH_3}{\overset{CH_3}{>}}C=\underset{CH_2-C_6H_5}{N}$ | 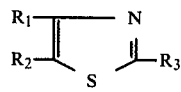 | 35% |
| $\underset{CH_3}{\overset{C_6H_5-CH_2}{>}}C=\underset{CH_3}{N}$ | $C_6H_5-CH_2\underset{S}{\overset{\phantom{xx}N\phantom{xx}}{\diagdown\phantom{x}\diagup}}$ + $\underset{C_6H_5}{\overset{CH_3}{>}}\underset{S}{\overset{\phantom{xx}N\phantom{xx}}{\diagdown\phantom{x}\diagup}}$ | 38%(total) |
| $\underset{CH_3CH_2}{\overset{H}{>}}C=\underset{CH_3}{N}$ | 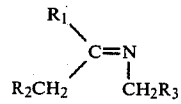 | 17% |

We claim:
1. A process for the preparation of a compound having the formula

$$R_1\underset{R_2\diagdown\phantom{x}\diagup S}{\overset{\phantom{xx}N\phantom{xx}}{\phantom{xxx}}}R_3$$

wherein $R_1$, $R_2$ and $R_3$ are independently hydrogen, loweralkyl, phenyl or substituted phenyl wherein the substituent is one or two of loweralkyl or halogen, which comprises reacting an imine having the formula:

$$\underset{R_2CH_2}{\overset{R_1}{>}}C=\underset{CH_2R_3}{N}$$

wherein $R_1$, $R_2$ and $R_3$ are as defined above, with sulfur dioxide in the presence of a catalyst consisting of a mixture of from 0.1 to 2% by weight of zirconium oxide, from 85 to 98% by weight of an alkaline earth metal oxide and from 1 to 15% by weight of an alkali metal hydroxide.

2. The process of claim 1 wherein the catalyst consists of 89% by weight of an alkaline earth metal oxide; 10% by weight of an alkali metal hydroxide, and 1% by weight of zirconium oxide.

3. The process of claim 2 wherein the catalyst consists of 89% by weight of calcium oxide, 10% by weight of sodium hydroxide and 1% by weight of zirconium oxide.

4. The process of claim 1 wherein the reaction is maintained at a temperature of from 400°–500° C.

5. The process of claim 4 wherein the reaction is maintained at a temperature of from 440°–480° C.

6. The process of claim 5 wherein the reaction is maintained at a temperature of about 460° C.

7. The process of claim 1 wherein from 10 moles of the imine is used for each mole of sulfur dioxide to 1 mole of the imine for 10 moles of sulfur dioxide.

8. The process of claim 1 wherein substantially equimolar amounts of the imine and sulfur dioxide are used.

9. The process of claim 1 wherein the imine and sulfur dioxide are present in the reaction stream at from 2–12 mole percent of each component.

10. The process of claim 9 wherein the imine and sulfur dioxide are present in the reaction stream at about 8 mole percent of each component.

11. The process of claim 1 wherein the product is 4-methylthiazole.

* * * * *